United States Patent
Jeon et al.

(10) Patent No.: US 10,647,627 B2
(45) Date of Patent: May 12, 2020

(54) METHOD FOR UPGRADING HYDROCARBON USING C4, C5 AND C6 STREAMS

(71) Applicants: SK Innovation Co., Ltd., Seoul (KR); SK Energy Co., Ltd., Seoul (KR)

(72) Inventors: Hee-Jung Jeon, Daejeon (KR); Yong-Woo Kim, Daejeon (KR)

(73) Assignees: SK Innovation Co., Ltd., Seoul (KR); SK Energy Co., Ltd., Seoul (KR)

( * ) Notice: Subject to any disclaimer, the term of this patent is extended or adjusted under 35 U.S.C. 154(b) by 6 days.

(21) Appl. No.: 14/887,929

(22) Filed: Oct. 20, 2015

(65) Prior Publication Data
US 2016/0115093 A1 Apr. 28, 2016

(30) Foreign Application Priority Data
Oct. 23, 2014 (KR) ........................ 10-2014-0144113

(51) Int. Cl.
| | |
|---|---|
| C07C 2/12 | (2006.01) |
| C07C 2/72 | (2006.01) |
| C10G 50/00 | (2006.01) |
| C10G 57/02 | (2006.01) |
| C10G 57/00 | (2006.01) |
| C10G 29/20 | (2006.01) |
| C10G 35/00 | (2006.01) |
| C10G 11/18 | (2006.01) |
| C07C 2/66 | (2006.01) |

(52) U.S. Cl.
CPC .................. *C07C 2/12* (2013.01); *C07C 2/66* (2013.01); *C07C 2/72* (2013.01); *C10G 11/18* (2013.01); *C10G 29/205* (2013.01); *C10G 35/00* (2013.01); *C10G 50/00* (2013.01); *C10G 57/005* (2013.01); *C10G 57/02* (2013.01); *C07C 2529/06* (2013.01); *C10G 2300/1088* (2013.01); *C10G 2300/301* (2013.01); *C10G 2300/302* (2013.01); *C10G 2300/304* (2013.01)

(58) Field of Classification Search
CPC ......... C07C 2/54–72; C07C 2/12; C07C 2/66; C07C 2529/06; C10G 57/005; C10G 29/205; C10G 11/18; C10G 57/02; C10G 35/00; C10G 50/00; C10G 2300/302; C10G 2300/1088; C10G 2300/301; C10G 2300/304
USPC .......................................................... 585/323
See application file for complete search history.

(56) References Cited

U.S. PATENT DOCUMENTS

| | | | | |
|---|---|---|---|---|
| 5,017,279 | A * | 5/1991 | Oswald .................. | C10G 50/02 208/18 |
| 2006/0199985 | A1* | 9/2006 | Kuechler ............... | C10G 50/00 585/1 |
| 2007/0282143 | A1* | 12/2007 | Driver ...................... | C07C 2/66 585/24 |
| 2008/0161621 | A1* | 7/2008 | Riley ......................... | C07C 2/66 585/468 |
| 2011/0147263 | A1* | 6/2011 | Umansky ............. | C10G 29/205 208/15 |
| 2013/0180884 | A1 | 7/2013 | Minoux et al. | |
| 2013/0225459 | A1* | 8/2013 | Bagheri .................. | C07C 11/02 508/110 |
| 2013/0253239 | A1* | 9/2013 | Bozzano ................... | C07C 2/06 585/256 |
| 2013/0299389 | A1* | 11/2013 | Garcia-Martinez ...... | B01J 20/18 208/113 |
| 2017/0211001 | A1* | 7/2017 | De Wet .................. | C10G 57/00 |

FOREIGN PATENT DOCUMENTS

EP 0439865 A1 8/1991

OTHER PUBLICATIONS

Giuseppe et al., "Oligomerization of olefins from Light Cracking Naphtha over zeolite-based catalyst for the production of high quality diesel fuel", Microporous and Mesoporous Materials, Jul. 20, 2012, pp. 127-134, vol. 164.

* cited by examiner

*Primary Examiner* — Ali Z Fadhel
(74) *Attorney, Agent, or Firm* — The Webb Law Firm

(57) ABSTRACT

The present disclosure relates to a method for upgrading hydrocarbon using C4, C5 and C6 streams, and more specifically, to a method for upgrading hydrocarbons using C4, C5 and C6 streams. The method includes the steps of: preparing C4, C5 and C6 streams, which are the products of naphtha catalytic cracking (NCC) process, heavy oil upgrading process, thermal cracking process, or fluidized catalytic cracking (FCC or RFCC) process; oligomerizing the C4, C5 and C6 streams with a catalyst to produce branched unsaturated hydrocarbons; and fractional distillating the branched unsaturated hydrocarbons to separate into C14-18 products or C32-40 products.

5 Claims, No Drawings

METHOD FOR UPGRADING HYDROCARBON USING C4, C5 AND C6 STREAMS

CROSS REFERENCE TO RELATED APPLICATION

This application claims priority to Korean Patent Application No. 10-2014-0144113 filed Oct. 23, 2014, the disclosure of which is hereby incorporated in its entirety by reference.

BACKGROUND

1. Technical Field

The present disclosure relates to a method for upgrading hydrocarbon using C4, C5 and C6 streams.

2. Description of the Related Art

Residue Fluidized catalytic cracking (RFCC) process is a process for producing LPG, gasoline, diesel, naphtha, etc. by fractionating a crude oil, is and then catalytic cracking a heavy residual oil remaining after the fractionation. Heavy residual oil itself do not include a fuel, and so it may be further cracked to produce LPG, gasoline, diesel, etc., which is referred to as a ground oilfield, one of the major oil companies advanced equipment.

Products that can be obtained through the RFCC process may include a wide range of materials, such as LPG, gasoline, diesel, etc., according to their boiling points, but the main target product has been gasoline to date. The yield of gasoline in the current RFCC process is around 50% by weight, and considering MTBE and alkylates produced from C4 product obtained through RFCC process, the gasoline yield may be more than 60% by weight.

However, with a reduced gasoline demand and a development of alternative energy sources for shale gas based gasoline, gasoline prices are falling steadily, and these trends are expected to intensify in the future.

Due to these trends, it is required that the target material in the RFCC process be changed by other materials in place of gasoline, and diesel may practically be considered as a faster alternative.

Typically, in RFCC process, C4 product has been used to produce C8 alkylates by reacting selectively separated iso-C4 paraffins with MeOH to afford MTBE, and then alkylating remaining C4 mixtures. Specifically, in RFCC process, C4 derived MTBE was used as an additive for gasoline, and C8 alkylates were used as a higher grade of gasoline. In other words, C4 product in RFCC process may be thought of as converted into gasoline by the reaction.

However, as described above, due to the increase in the gasoline supply and the reduction in the gasoline demand, the price of gasoline becomes increasingly lower, and so it is expected that these trends will become increasingly more severe. Therefore, considering these trends, the current methods of converting RFCC C4 products into MTBE and C8 alkylates and applying same to gasoline are problematic, and so there exists a need to increase the economic efficiencies by modifying the objects and the methods to those producing other higher valuable compounds.

Generally, C5 and C6 products in RFCC process are also included in the area of gasoline and used as a gasoline, as classified according to their boiling points. But the octane numbers of C5 and C6 products in RFCC process are too low for use as gasoline. Currently, since there is no technique for converting the C5 and C6 products in RFCC process into high value materials, C5 and C6 products in RFCC process are in use as gasoline with lower octane numbers.

Likewise, problems and needs as described above have also occurred to the products from, in addition to the RFCC process, for example, such as naphtha cracking process, heavy oil upgrading process, thermal cracking process, etc.

BRIEF SUMMARY OF THE INVENTION

The technical problems of the present disclosure for which the present disclosure is intended to solve are not limited to those mentioned above, and other technical problems will be clearly understood by those skilled in the art from the following descriptions.

An object of the present disclosure is to provide a method for upgrade hydrocarbons using C4, C5 and C6 streams in view of the recent changes in demand and the above-mentioned problems.

In accordance with an aspect of the present disclosure, provided is a method for upgrading hydrocarbons using C4, C5 and C6 streams, comprising: preparing C4, C5 and C6 streams, which are the products of naphtha catalytic cracking (NCC) process, heavy oil upgrading process, thermal cracking process, or fluidized catalytic cracking (FCC or RFCC) process; oligomerizing the C4, C5 and C6 streams with a catalyst to produce branched unsaturated hydrocarbons; and fractional distillating the branched unsaturated hydrocarbons to separate into C14-18 products or C32-40 products.

According to some embodiments of the present disclosure, the upgraded products of C4, C5 and C6 streams have effects as follows in terms of the branched unsaturated hydrocarbons.

C14-18 products have a flash point of greater than or equal to 85° C., a pour point of less than −5° C., and a specific gravity of 0.77 to 0.81; do not contain sulfur, nitrogen, and aromatic compounds; and can be used as diesels in the form of branched hydrocarbons. Especially, since such diesels have a very low pour point, and do not contain aromatics, when they are applied to drilling oils, high-quality of drilling oils can be obtained.

C32-40 products have a low viscosity index and a low pour point. For this reason, in order to use as lubricant base oil, C32-40 products may be simply mixed with inexpensive hydrocarbons which are able to complement the low viscosity index, to produce the lubricant base oil, which therefore provides a higher effect on the process efficiency.

That is, in skeletal isomerization process, known as a conventional lubricant base oil manufacturing process, linear paraffins were modified by shifting the end carbons in the hydrocarbon chain to create a branched configuration. Meanwhile, in the present disclosure, the upgraded products of C4, C5 and C6 streams are branched hydrocarbons which have a low viscosity index and a low pour point. Therefore, according to some embodiments of the present disclosure, lubricant base oil can be produced by simply mixing inexpensive hydrocarbons without using the skeletal isomerization process where the process conditions are complex, which is accordingly provides a higher effect on the process efficiency.

In addition, the upgraded products of C4, C5 and C6 streams according to some embodiments of the present disclosure are branched unsaturated hydrocarbons, and then can be modified to produce a new type of alkyl aromatic compounds through aromatic alkylation process, which therefore can provide advantages of replacing the existing alkyl aromatic compounds.

DETAILED DESCRIPTION

Advantages and features of the present disclosure and methods of accomplishing the same reference to the following detailed description of exemplary embodiments will be apparent. However, the present disclosure will be embodied in many different forms and is not limited to the embodiments set forth below, but the present embodiment is that so as to complete the disclosure of the present disclosure, ordinary skill in the art—environment to be provided to fully convey the concept of the invention to those, the present disclosure will only be defined by the appended claims. As used herein, the singular forms "a," "an" and "the" include plural referents unless the context clearly dictates otherwise.

Hereinafter, exemplary embodiments of the present disclosure will be described.

According to an aspect of the present disclosure, a process for upgrading hydrocarbons using C4, C5 and C6 streams includes preparing C4, C5 and C6 streams; oligomerizing the C4, C5 and C6 streams with a catalyst to produce branched unsaturated hydrocarbons; and fractional distillating the branched unsaturated hydrocarbons to separate into C14-18 products or C32-40 products.

First, the method of the present disclosure includes preparing C4, C5 and C6 streams.

Raw materials C4, C5 and C6 that can be used in the process of the present disclosure may include, but are not limited to, products of cracking process, such as naphtha catalytic cracking (NCC) process, heavy oil upgrading process, thermal cracking process, or fluidized catalytic cracking (FCC or as RFCC) process.

Next, the method of the present disclosure includes oligomerizing the C4, C5 and C6 streams with a catalyst to produce branched unsaturated hydrocarbons.

Here, the branched unsaturated hydrocarbons are of branched internal olefins (BIO), which can produce a new type of alkyl aromatic compounds by aromatic alkylation process to be described later, and thereby can replace the existing alkyl aromatic compounds.

In the oligomerization process, the reaction conditions and the process that can be applied thereto may vary depending on the carbon numbers of the products. Hereinafter, a process for upgrading hydrocarbons depending on the carbon numbers of the products will be described.

Oligomerization for C14-18 Products and Others

According to some embodiments, the oligomerixation of C4, C5 and C6 to obtain C14-18 products may be carried out at a reaction temperature of 10 to 200° C., more preferably 80 to 200° C., and under pressure of 10 to 90 bars, more preferably of 10 to 60 bars. For a continuous oligomerization of gaseous reactants, polar solvents, such as anhydrous toluene, may be introduced.

When the reaction temperature is greater than 200° C., the molecular weight increasing reaction activity by the C4-C6 products becomes high, and the yield of high molecular weight materials rendering difficult for use in drilling oils increases, while when the reaction temperature is less than 10° C., reaction activity itself is lowered. Although not significantly influenced by the reaction pressure, when the reaction pressure is high, the mobility of molecules becomes decreased, and the activity becomes lowered. Under the reaction conditions, since C4-C6 products may be converted into gases, polar solvents, such as toluene, may be further introduced. Toluene may be preferably used in the absence of water. C4-C6 gases are dissolved into toluene so introduced, and toluene induces a polymerization reaction on the catalyst present in the solution, thereby increasing the efficiency of the polymerization reaction.

Catalysts that may be used in the oligomerization of C4, C5 and C6 to obtain C14-18 products preferably include metallocene-based catalyst, such as zeolite.

Products produced from the reaction may contain at least 10% by weight of C14 or more branched hydrocarbons, and more preferably at least 50% by weight of C14 or more branched hydrocarbons.

In the process of the oligomerization of C4, C5 and C6, hard materials, i.e., C4, C5 and C6 saturated hydrocarbons may be created. In this embodiment, the C4, C5 and C6 saturated hydrocarbons are separated, and then the separated C4, C5 and C6 saturated hydrocarbons are partially dehydrogenated to produce C4, C5 and C6 unsaturated hydrocarbons. The C4, C5 and C6 unsaturated hydrocarbons are further mixed with the C4, C5 and C6 streams for oligomerization reaction (recycling), such that the yield of the C14-18 products can be increased.

In this embodiment, however, since the contents of the C4, C5 and C6 saturated hydrocarbons are not so high, they may be applied as a raw material as they are without being separated and leave unreacted, which then may be separated later, and applied as LPG fuels. Therefore, the partial dehydrogenation route may be optional.

C14-18 products generated by the oligomerization reaction may have a boiling point of 190 to 340° C., and may be separated by fractional distillation process.

C14-18 products of the present disclosure may have a flash point of greater than or equal to 85° C., a pour point of less than −5° C., and a specific gravity of 0.77 to 0.81. The C14-18 products of the present disclosure do not contain sulfur, nitrogen and aromatics, and may be used as diesels in the form of branched hydrocarbons. Especially, since such diesels have a very low pour point, and do not contain aromatics, when they are applied to drilling oils, high-quality of drilling oils can be obtained.

On the other hand, the method of the present disclosure may further include carrying out aromatic alkylation reaction with the C14-18 products.

The aromatic alkylation reaction may be Friedel-Craft alkylation reaction. The C14-18 products may be produced at a reaction temperature of 170 to 300° C. under a pressure of 1 to 50 bars in inert conditions, such as $N_2$, for a reaction time of 2 to 48 hrs. The catalyst used is a cationic catalyst, and may be selected from zeolite, clay, etc. Since strong acid material may induce side reactions such as olefin oligomerization, a catalyst system which can intentionally lower the acidity is or optionally reduce the use of strong acid may be used. Steamed USY zeolite, RE-metal partially substituted zeolite, etc. may be used, and acid catalyst may also be used. When using the acid catalyst, the reaction may be carried out at a temperature of 10 to 250° C. under inert conditions. When using the acid catalyst, since browning of raw materials may not be completely prevented, use of a cationic catalyst is more preferred.

A new type of alkyl aromatic compounds obtained by aromatic alkylation reaction may replace the existing alkyl aromatic compounds.

These alkyl aromatic compounds so obtained show excellent low temperature properties as compared to the conventional alkyl aromatic compounds. For example, since the conventional alkyl naphthalene was prepared by the alkylation of a linear alpha olefin (LAO) and naphthalene, its limit to lower the pour point was present.

However, in the case of the present alkyl naphthalene produced by the alkylation of naphthalene with a branched unsaturated hydrocarbon, its pour point degradation properties are very high. This is because the branched unsaturated hydrocarbons are used instead of linear alpha unsaturated hydrocarbons. Moreover, the linear alpha unsaturated hydrocarbons are prepared by the polymerization of ethylene from a full range of linear alpha olefins (LAO) process. These LAO are compounds is prepared by a full range of LAO process, and therefore they are relatively expensive. However, since the C4, C5 and C6 products (b.p. <78° C.) prepared by RFCC process may be used as a fuel, the price of the branched unsaturated hydrocarbons derived from the simple oligomerization process only are relatively very low, and incomparably many stocks exist. In other words, it is possible to proceed the branched unsaturated hydrocarbons chemistry on their own.

Oligomerization for C32-40 Products and Others

According to some embodiments, the oligomerization of C4, C5 and C6 to obtain C32-40 products may be carried out using a solvent, such as toluene, at a reaction temperature of 170 to 300° C., more preferably 200 to 300° C., and under pressure of 10 to 90 bars, more preferably of 10 to 60 bars.

When the reaction temperature is greater than 300° C., the molecular weight increasing reaction activity becomes high, and side reaction materials, such as aromatic compounds, are mass produced. When the reaction temperature is less than 170° C., the reaction activity itself is lowered. Although not significantly influenced by the reaction pressure, when the reaction pressure becomes higher, the mobility of molecules becomes decreased, and the reaction activity becomes lowered. The products may be in a gaseous state at the operating conditions. Thus, since the reaction may substantially be a polymerization reaction in gas phase, and only the amount dissolved in a solvent, such as toluene, can participate in the reaction, the participation of the products into the reaction cannot but be extremely limited. However, since, as the reaction proceeds, a steric hindrance gradually becomes large, and the reaction hardly proceeds, the oligomerization reaction under severe conditions is unavoidable. Of course, this is a result that corresponds to the zeolite catalyst and clay catalyst system. When high molecular weight polymerization catalysts having a single strong acid point, such as metallocene, are used, the reaction may proceed even at a lower temperature of less than or equal to 60° C.

Preferably, the catalysts that may be used in the oligomerization reaction to obtain C32-40 products may include a metallocene-based catalyst, such as zeolite.

The products generated through the reaction may include 10% by weight or more, and more preferably 50% by weight or more of C32-40 branched hydrocarbons.

The C32-40 products created by the oligomerization reaction have a boiling point of greater than or equal to 340° C., and can be isolated by vacuum distillation.

The method of the present disclosure may further include mixing the C32-40 products with low cost hydrocarbons. The C32-40 products have a low viscosity index and a low pour point. For this reason, in order for C32-40 products to use as lubricant base oil, the low cost hydrocarbons that can complement the low viscosity index may be further mixed therewith.

That is, in skeletal isomerization process, known as a conventional lubricant base oil manufacturing process, linear paraffins were modified by shifting the end carbons in the hydrocarbon chain to create a branched configuration.

Meanwhile, in the present disclosure, the upgraded products of C4, C5 and C6 streams are branched hydrocarbons which have a low viscosity index and a low pour point. Therefore, according to the present disclosure, lubricant base oil can be produced by simply mixing inexpensive hydrocarbons without using the skeletal isomerization process where the process conditions are complex, which accordingly provides a higher effect on the process efficiency.

More specifically, C32-40 products may be mixed with low-cost hydrocarbons to produce lubricant base oil.

The C32-40 products per se may not be employed as lubricant base oil. This is because a plenty of branches are present in their molecules, and so the viscosity index is too low, although the pour point is highly advantageous. That is, in order for C32-40 products to use as lubricant base oil, hydrocarbons having a high viscosity index must be incorporated thereinto to balance the properties, and therefore the present disclosure may include mixing low cost hydrocarbons.

The low cost hydrocarbons in the present disclosure may be selected such that they serve to complement the properties of C32-40 products to be used as lubricant base oil. In this regard, preferably, the low cost hydrocarbons may have a carbon number of 32 to 70, a viscosity index of at least 145, a pour point of at least 10° C., and a viscosity index at 100° C. of at least 4 cPs.

Preferably, the mixing ratio of C32-40 products to the low cost hydrocarbons may be in a range of from 1:0.1 to 20. The mixing ratio may be controlled based on the viscosity index at 100° C. and the pour point for the final lubricant base oil. In order to meet the desired properties, the mixing ratio may be adjusted. When the ratio of the C32-40 products is too high, a low cost hydrocarbon having a very high viscosity index is required, but it is difficult to obtain such a low cost hydrocarbon. In contrast, when the ratio of C32-40 products is too low, it becomes difficult to meet the pour point characteristic. In this way, desired properties suitable for lubricant base oil may be tailored by selecting the properties of the lubricant base oil, and adjusting the mixing ratio of the C32-40 products and the low cost hydrocarbons.

On the other hand, the method of the present disclosure may further include carrying out the aromatic alkylation reaction with the resulting C32-40 products.

The aromatic alkylation reaction may be carried out at a reaction temperature of 150 to 350° C. under $N_2$ 1 to 20 bars for 0.5 to 48 hrs at 200 to 7000 rpm using an acid catalyst, such as zeolite, in a batch reactor. The resulting materials may be selectively separated via vacuum distillation, and the analysis in viscosity index and pour point to apply lubricant additives may be conducted.

This new type of alkyl aromatic compounds obtained by the aromatic alkylation reaction may replace the existing alkyl aromatic compounds.

According to some embodiments of the present disclosure, the raw material, C6 stream has preferably a boiling point of less than 78° C. When the boiling point is higher than 78° C., since benzene may be included in the reaction, the resulting product may not be applied as lubricant base oil.

Hereinafter, representative embodiments for implementing an object of the present disclosure will be described in more detail by way of illustrative examples. However, the scope of the present disclosure is not limited to these examples.

EXAMPLE 1

797 g of LCN product obtained from RFCC process was introduced into a fractional distillation column and cut at 73°

C. to afford 157.3 g of product. While flushing autoclave with $N_2$, a mixture of 300 cc of toluene free of water via Na and 25.1 g of zeolite calcined for 3 hrs at 550° C. was slowly introduced into the autoclave. Then, 157.3 g of the product was slowly introduced into the autoclave as flushed with $N_2$. Then, C4 product obtained from RFCC process was introduced to charge up to 20 bars of reaction pressure. Then, the autoclave was locked. The mixture was slowly stirred at 300 rpm, elevated to the temperature of 180° C., and then maintained for 3 hrs. After the reaction was completed, the reactor was lowered to room temperature and atmospheric pressure. Then, gaseous products were collected separately, zeolite used for filter was removed, and then the remaining liquid products were recovered for SimDist analysis. The weight of the recovered liquid products was 421.3 g. The results are shown in Table 1 below.

TABLE 1

| Product | Yield (wt %) |
|---|---|
| Feed (bp < 78° C.) | 16 |
| Product A (bp 78~170° C.) | 71 |
| Product B (bp 170~190° C.) | 7 |
| Product C (bp 190~343° C.) | 5 |
| Product D (bp > 343° C.) | 1 |

TAH analysis to check the content of aromatic compounds relative to the product confirmed that small amount of 2.8% by weight of the aromatic compounds was contained. The above products were cut at 220° C. to obtain 17.1 g of materials. The remaining was again recycled to the autoclave. Again 25.1 g of zeolite and 30 cc of toluene were further introduced. Likewise, C4 product was introduced to adjust up to 20 bars, and then the same experiment was repeated. Then, the materials corresponding to 220 to 343° C. through cut based on the boiling point were collected. In this way, the materials corresponding to 53.5 g of diesel were collected. TAH analysis for the content of the aromatic compounds confirmed that the aromatic compounds were slightly lowered to amount of 2.3% by weight.

EXAMPLE 2

53.5 g of materials having a boiling point of 220 to 343° C. recovered from Example 1 and 130.1 g of naphthalene were introduced into 500 cc autoclave. 9.5 g of USY zeolite (CBV 712, Saint-Gobain) was introduced, and flushed with $N_2$. Then, the autoclave was locked, and the reaction temperature was raised to 180° C., and then was maintained for 3 hours. After the reaction was completed, the products were recovered as n-heptanes, and zeolites and unreacted naphthalenes were separated. The reactor was held at 85° C. and 100 mmHg with rotary evaporator, and n-heptanes were selectively removed. 78.3 g of liquid products were recovered for SimDist analysis. The results are shown in Table 2 below.

TABLE 2

| SimDst analysis | Yield (wt %) |
|---|---|
| Product A(216~220° C.) | 4 |
| Product B(190~343° C.) | 22 |
| Product C (380~480° C.) | 69 |
| Product D(>480° C.) | 5 |

Product A was estimated as naphthalenes, Product B was estimated as unreacted branched unsaturated hydrocarbons, and Product C was estimated as alkyl naphthalenes. Product D confirmed as having a high molecular weight was estimated as a material in which two or more branched internal olefins were combined.

Product C was separated using fractional distillation (Spaltrohr HMS 300 C Equipment; Fischer technology), and the pour point of the Product C was determined to confirm the low temperature lubrication properties. The results are shown in Table 3 below.

TABLE 3

| Estolide | Viscosity at 40° C. (cSt) | Viscosity at 100° C. (cSt) | Viscosity Index | Pour point (° C.) | Iodine value (cg/g) |
|---|---|---|---|---|---|
| Product C | 18.89 | 3.72 | 68.8 | −37 | 0.01 |

It was confirmed that although the viscosity index was somewhat low, the pour point was very low, and therefore the material was available for use as a good pour point depressants.

EXAMPLE 3

The same procedure was repeated as Example 1, except that the reaction temperature was elevated to 220° C. and the fractional distillation (Spaltrohr HMS 300 C Equipment; Fischer technology) was employed, to obtain 83.3 g of materials having a boiling point of 340° C. or more. In order to confirm the suitability of the recovered materials as lubricant base oil, the materials were analyzed to determine the properties. The results are shown in Table 4 below.

TABLE 4

| Properties | Analysis Values |
|---|---|
| Viscosity (40° C.) | 5.88 |
| Viscosity (100° C.) | 44.52 |
| Viscosity Index | 60.2 |
| Pour point (° C.) | <−50° C. |
| Sulfur (ppm) | 0.01 |
| TAH | N.D. |

Analysis indicated that the materials advantageously had a very low pour point, while the viscosity index was 60.2 which could not be used directly as lubricant base oil.

Thus, lubricant base oil could be prepared by way of mixing a by-product, UCO from UC hydroprocessing. The properties of the lubricant base oils according to the mixing ratios of alkylates and low cost hydrocarbons are presented in Table 5 below.

TABLE 5

| | Mixing ratios (alkylates:low cost hydrocarbons) | | | | |
|---|---|---|---|---|---|
| | 1:0 | 3:1 | 45:55 | 1:3 | 0:1 |
| Viscosity (40° C.) | 5.88 | 5.81 | 5.63 | 5.54 | 5.39 |
| Viscosity (100° C.) | 44.52 | 40.02 | 33.70 | 28.13 | 22.15 |
| Viscosity Index | 60.2 | 79.9 | 105.1 | 138.7 | 194.1 |
| Pour point (° C.) | <−50 | −36.2 | −22.6 | −1.3 | 13.0 |
| Sulfur (ppm) | 0.01 | 0.01 | 0.01 | 0.01 | 0.01 |
| TAH | N.D. | N.D. | N.D. | N.D. | N.D. |

It was confirmed that when the alkylates and low cost hydrocarbons were mixed in a ratio of 45:55, the lubricant base oil having viscosity index 105 and pour point −22° C.

could be obtained. The viscosity index was somewhat lower than the standards of the typical lubricant base oil. The low viscosity index could be further complemented using the by-product of UC process having a little higher viscosity index.

While the invention has been described with respect to the above specific embodiments, it should be recognized that various modifications and changes may be made to the invention by those skilled in the art which also fall within the scope of the invention as defined by the appended claims.

What is claimed is:

1. A method for oligomerizing $C_4$, $C_5$ and $C_6$ hydrocarbon streams comprising:

preparing $C_4$, $C_5$ and $C_6$ hydrocarbon streams in a Residue Fluidized Catalytic Cracking (RFCC) process;

oligomerizing the $C_4$, $C_5$ and $C_6$ hydrocarbon streams with a catalyst to produce branched unsaturated hydrocarbons;

separating the branched unsaturated hydrocarbons in a fractional distillation column to separate a first fraction comprising $C_{14}$-$C_{18}$ branched unsaturated hydrocarbons and a second fraction comprising $C_{32}$-$C_{40}$ branched unsaturated hydrocarbons; and subjecting the $C_{32}$-$C_{40}$ branched unsaturated hydrocarbons in the second fraction to aromatic alkylation at a temperature of 150 to 350° C. to produce a second alkylaromatic product having a pour point of less than −50° C.

2. The method of claim 1, wherein the oligomerization is carried out at reaction temperature of 80 to 200° C. and under pressure of 10 to 60 bars, and the method further comprises separating $C_4$, $C_5$ and $C_6$ saturated hydrocarbons produced by the oligomerization reaction; partially dehydrogenating the separated $C_4$, $C_5$ and $C_6$ saturated hydrocarbons to produce $C_4$, $C_5$ and $C_6$ unsaturated hydrocarbons; and mixing the $C_4$, $C_5$ and $C_6$ unsaturated hydrocarbons with the $C_4$, $C_5$ and $C_6$ hydrocarbon streams.

3. The method of claim 1, wherein the oligomerization reaction is carried out at a temperature of 200 to 300° C. and under pressure of 10 to 90 bars.

4. The method of claim 1, wherein $C_{32}$-$C_{40}$ products have a boiling point of 340° C. or more.

5. The method of claim 1, wherein the catalyst is a zeolite, a cationic catalyst (clay), an acid catalyst, or a metallocene-based catalyst.

* * * * *